United States Patent [19]

Herlihy et al.

[11] Patent Number: 4,546,096

[45] Date of Patent: Oct. 8, 1985

[54] ANTICHOLINERGIC GLUCURONIDES AND ANTIPERSPIRANT USE THEREOF

[75] Inventors: Walter C. Herlihy; David M. Epstein, both of Middlesex County, Mass.; Carl B. Felger, Prince George County, Md.

[73] Assignees: Repligen Corporation, Cambridge; The Gillette Company, Boston, both of Mass.

[21] Appl. No.: 583,111

[22] Filed: Feb. 24, 1984

[51] Int. Cl.$^4$ ...................... A61K 31/70; C07H 15/00
[52] U.S. Cl. ..................................... 514/25; 536/17.4; 536/17.9; 536/18.2; 546/268
[58] Field of Search ............................. 536/17.4, 18.2; 546/268; 424/180; 514/25

[56] References Cited

U.S. PATENT DOCUMENTS

| | | | |
|---|---|---|---|
| 3,624,200 | 11/1971 | Moffett | 424/65 |
| 3,767,786 | 10/1973 | MacMillan | 424/65 |
| 4,471,111 | 9/1984 | Herlihy | 536/17.4 |
| 4,476,300 | 10/1984 | Herlihy et al. | 536/17.4 |

OTHER PUBLICATIONS

MacMillan, "Chem. Abst.", vol. 67, 1967, p. 32874(n).

Primary Examiner—Johnnie R. Brown
Attorney, Agent, or Firm—Roman Saliwanchik

[57] ABSTRACT

This invention concerns novel and useful human antiperspirant compounds which are glucuronides of phenolic anticholinergics or the phenolic derivatives of anticholinergic compounds. These antiperspirant compounds, advantageously, do not have mydriatic properties possessed by the parent anticholinergic compounds.

17 Claims, No Drawings

ANTICHOLINERGIC GLUCURONIDES AND ANTIPERSPIRANT USE THEREOF

BACKGROUND OF THE INVENTION

Anticholinergic compounds are well known for their property of controlling perspiration. U.S. Pat. Nos. 3,624,200 and 3,767,786 disclose and claim processes for controlling perspiration with scopolamine esters.

It is well known that anticholinergic compounds have a mydriatic effect. This mydriatic effect, though desirable in conjunction with an eye examination by an eye doctor, is an undesirable property for an antiperspirant because an accidental transfer of an anticholinergic antiperspirant to the eye can represent a significant safety problem.

As exemplified by the above-mentioned U.S. patents, the predominant anticholinergics made for antiperspirant use are scopolamine and its esters. Though the efficacy of scopolamine and its esters was demonstrated over twenty years ago, it is apparent that these compounds have not achieved widespread use as antiperspirants. This lack of use may be related to the mydriatic property referred to above, and, additionally, to the fact that ester-containing anticholinergics such as scopolamine may be cleaved by esterase activity in human perspiration, thus rendering the anticholinergic ineffective as an antiperspirant. Also, despite the fact that scopolamine is a potent anticholinergic, its antiperspirant activity is too low for commercial use.

The problems of esterase inactivation and mydriasis, discussed above, have been overcome by the use of glucuronides of anticholinergic compounds. Examples of such glucuronides are tropicamide O-$\beta$-D-glucuronide and scopolamine O-$\beta$-D-glucuronide, shown in Chart I. The mydriatic effect of the anticholinergics was corrected by conversion to the glucuronide. The subject invention concerns novel glucuronide compounds of anticholinergics that are effectively hydrolyzed by human sweat glucuronidase. Exemplary of these compounds are the O-$\beta$-D-glucuronides of p-hydroxybenzoyl tropicamide and p-hydroxybenzoyl scopolamine. These compounds are hydrolyzed by sweat glucuronidase 20- to 80-fold more rapidly than the parent drug glucuronides. In addition, the p-hydroxybenzoyl glucuronides show no detectable mydriasis activity.

BRIEF SUMMARY OF THE INVENTION

Unexpectedly, we have discovered novel compounds that do not have mydriatic properties and that are converted to effective antiperspirants by the human sweat glucuronidase. The compounds of the subject invention are glucuronides of phenolic anticholinergics or the phenolic derivatives of anticholinergics. More specifically, the compounds of the invention are glucuronides of anticholinergic compounds that inherently possess a phenolic moiety, or anticholinergic compounds in which the phenolic moiety is introduced by suitable derivatization. Examples of these compounds are p-hydroxybenzoyl scopolamine p-hydroxybenzoyl tropicamide: para, meta, or ortho hydroxylated derivatives of scopolamine, atropine, scopolamine N-oxide, eucatropine, homatropine, procyclidine, and the like: para, meta, ortho hydroxylated derivatives of fatty acid esters of scopolamine, for example, O-benzoyl p-hydroxyscopolamine, n-hexanoyl p-hydroxyscopolamine, 2-ethylbutyrl p-hydroxyscopolamine N-oxide, and the like.

DETAILED DESCRIPTION OF THE INVENTION

Initially, there are disclosed general conditions for the enzymatic reaction, isolation processes, and procedures used to test the invention compounds for efficacy as antiperspirants. The preparation of the compounds, and their antiperspirant formulation, are disclosed in the examples that follow.

The enzymatic reaction, described herein, can be carried out over a pH range of about 7 to about 8.5, with different buffer strengths and with various buffers, for example, sodium N-2-hydroxyethyl piperazine-N'-2-ethanesulfonic acid, tris hydrochloride, and the like.

The chromatographic methods described herein are based on reversed phase liquid chromatography on C-18 silica supports. This technique is well suited for the purification of enzymatically-produced glucuronides of hydrophobic compounds. Unreacted aglycon is much more hydrophobic than the corresponding glucuronide and thus will be well resolved on reversed phase systems. The cofactor, UDP glucuronic acid, the enzymes, and the byproduct, UDP, are all very hydrophilic and will be much less retained than the glucuronide of a hydrophobic compound. Finally, all the solvent systems described are based on ammonium acetate, an easily removable buffer. Modifications to this system may be necessary in order to purify glucuronides of very hydrophilic compounds. Other reversed phase stationary supports, for example, phenyl silica, C-8 silica, and the like, can be used.

Liver microsomes, which can be used in the subject invention, can be obtained from mammalian sources, for example, rabbit, bovine, and the like.

The temperature of incubation in the enzymatic step can be from about 20° to about 45° C.

METHODS FOR TESTING AND CHARACTERIZING THE COMPOUNDS OF THE SUBJECT INVENTION

Preparation of $\beta$-glucuronidase from human sweat

Sweat was obtained from human volunteers by collection from the axilla during high temperature (>41° C.) in a sauna. The sweat was clarified by centrifugation at 20,000 g for 30 min. This clarified sweat was then either utilized directly in hydrolysis studies or dialyzed against 100 mM NaCl, 50 mM sodium acetate, pH 5.0 prior to use. Dialysis increased the longevity of the enzyme activity as well as lowering the background of the HPLC chromatograms. Most of the data presented herein was generated with dialyzed preparations.

Determination of standard activity of human sweat $\beta$-glucuronidase $\beta$-glucuronidase activity was assayed in the sweat by hydrolysis of phenolphthalein glucuronide. Briefly, this assay was carried out as follows: to an aliquot of undialyzed sweat was added an equal volume of buffer comprising 100 mM NaCl, 100 mM sodium acetate, pH 5.0 (this step was unnecessary when assaying dialyzed sweat) followed by 10 µl of a 100 mg/ml phenolphthalein glucuronide solution (Sigma Chemical, St. Louis, Mo.). The reaction mixture was then incubated at 37° C. After 30 min an aliquot of the reaction mixture was added to a five-fold excess of a 0.2 M glycine buffer, pH 10.4 and the absorbance wa determined at 540 nm. The activity was determined by comparison to a known amount of *E. coli* β-glucuronidase (Sigma, Type VII) run under standard conditions. Activities ranging from 96–150 units/ml were found in the samples of sweat tested.

Hydrolysis of model glucuronides by human sweat glucuronidase

A variety of glucuronides were synthesized and tested for their ability to be hydrolyzed by human sweat glucuronidase. Included in this group were tropicamide and scopolamine glucuronide. These hydrolysis reactions were all carried out under similar conditions, and the extent of hydrolysis was determined at the various time points by HPLC analysis of the reaction mixture.

Generally, dialyzed preparations of sweat were used for the reasons discussed earlier. Similar results were obtained with undialyzed samples. A typical experiment was done by bringing the enzyme solution (50–100 U/ml) to 0.01 to 0.05% in the glucuronide to be tested. A zero time aliquot was withdrawn and stored frozen; the remaining reaction mixture was incubated at 37° C. Aliquots were taken at various time points for rate determinations. These aliquots were stored at −20° C. until analysis by HPLC.

Calculation of reaction rates

High pressure liquid chromatography of the aliquots drawn from the hydrolysis reactions allowed the separation of the aglycon from the glucuronide in all cases. The nmoles released at any given time were calculated from the absorption at 254 nm and the known extinction coefficient of the compound. Rates are given as initial rates which are determined by plotting nmoles aglycon vs. time.

Mydriasis assay conditions

The rabbit eye pupil diameter was measured with a clear plastic ruler after exposing the eye to 50 W light at a distance of 6 in. Exposure to light contracts the pupil to approximately 3 mm diameter.

The addition of the compounds to be tested is done in a maximum volume of 150 μl, in 50 mM $NaPO_4$, pH 6.8, 100 mM NaCl. The sample was applied in the upper corner of the eye and was allowed to completely cover the cornea after each addition. Pupil dilation was measured at 3 separate intervals following the procedure outlined above. Buffer controls were run in one eye and the anticholinergic in the other.

Specificity of human sweat β-glucuronidase

Table I shows relative hydrolysis rates of phenolphthalein glucuronide (PGA), tropicamide glucuronide and scopolamine glucuronide by three different β-glucuronidases: *E. coli*, bovine liver, and dialyzed human sweat. As indicated in Table I, enzyme activities were diluted so that the hydrolysis rates for PGA were equivalent. It is clear from this table that the *E. coli* enzyme rapidly hydrolyzes tropicamide glucuronide and has lower, but significant, activity for scopolamine glucuronide. The bovine enzyme, however, shows significant discrimination against the glucuronides of scopolamine or tropicamide. This discrimination is even more evident with the human sweat enzyme at pH 5.0, the optimal pH for the bovine enzyme. Trace amounts of tropicamide glucuronide were hydrolyzed, but no scopolamine could be detected. At pH 6.8, the optimal pH for the *E. coli* enzyme, no hydrolysis of either anticholinergic glucuronide is detectable therefore, further work with human sweat was carried out at pH 5.0.

Characterization of tropicamide p-hydroxybenzoyl O-β-D-glucuronic acid and scopolamine p-hydroxybenzoyl O-β-D-glucuronic acid As can be seen from the data in Table 2, tropicamide p-hydroxybenzoate and scopolamine p-hydroxybenzoate are potent mydriatic agents compared to the parent drugs. Tropicamide shows a weak response at 20 μg; whereas the p-hydroxybenzoate derivative is clearly mydriatic at 5.5 μg. Similarly, 0.6 μg of scopolamine is nonmydriatic but 0.1 μg of the p-hydroxybenzoate is sufficient for a response. The mydriatic activity of both scopolamine p-hydroxybenzoate and tropicamide p-hydroxybenzoate is blocked by formation of the corresponding glucuronide. No mydriatic response is seen for either scopolamine- or tropicamide p-hydroxybenzoyl glucuronide when administered at levels 100-fold greater than required to effect a strong mydriatic response with the aglycon.

The following examples are illustrative of the process and products of the invention, but are not to be construed as limiting. All percentages are by weight and all solvent mixture proportions are by volume unless otherwise noted.

EXAMPLE 1

Synthesis of Tropic Acid and p-Hydroxyphenylacetic Acid Methyl Esters

This example discloses the preparation of either tropic acid methyl ester or p-hydroxyphenylacetic acid methyl ester by use of either tropic acid or p-hydroxyphenylacetic acid as the respective starting material. The conditions of the process for making either ester are otherwise the same.

One gram of either DL-tropic acid (Sigma) or p-hydroxyphenylacetic acid (Aldrich Chemical Co., Milwaukee, WI) is combined with 1N HCl in methanol (1.5 ml) at 25° C. for one hr. Methanol and HCl are removed by evaporation in vacuo to yield a yellow residue. The methyl esters of tropic acid and p-hydroxyphenylacetic acid are resuspended in distilled water and identified by HPLC.

HPLC conditions are as follows: a 3.9 mm×30 cm μBondapak C18 column (Waters Associates, Inc., Milford, MA) is eluted at 2 ml/min with 0.1% $NH_4OAc$ (pH 7.5). After injection of the sample, a linear gradient to 60% methanol is applied to the column over a 20 min period. The column eluant is monitored at 254 nm. Under the HPLC conditions described above, the methyl ester of p-hydroxyphenylacetic acid elutes at 44% methanol while p-hydroxyphenylacetic acid elutes at 10%. Tropic acid methyl ester elutes at 48%, while the parent compound elutes at 12% methanol.

EXAMPLE 2

Synthesis of Tropic Acid Methyl Ester-O-β-D-Glucuronide and p-Hydroxyphenylacetic Acid Methyl Ester-O-β-D-Glucuronide (See Chart 3)

This example discloses the preparation of either tropic acid methyl ester-O-β-D-glucuronide or p-hydroxyphenylacetic acid methyl ester-O-β-D-glucuronide by use of either tropic acid methyl ester or p-hydroxyphenylacetic acid methyl ester as the respective starting material. The conditions of the process for making either glucuronide are otherwise the same.

Four gm of a rabbit liver or bovine liver microsomal fraction (Sigma) are suspended in 100 ml of a 75 mM tris hydrochloride buffer (pH 7.5–8.0). The microsomes are suspended by repeatedly drawing the mixture through a pipette tip. The microsomes are then pelleted by centrifugation at 100,000 g for 30 min. The supernatant is discarded, and the pellet is resuspended to 100 ml with a 150 mM tris hydrochloride, pH 7.5–8.0 solution, containing approximately 9 mM of tropic acid methyl ester or p-hydroxyphenylacetic acid methyl ester, and 1 gm of sodium uridine 5'-diphosphoglucuronic acid (UDPGA) (Sigma). After a 20 hr incubation at 37° C., the reaction is terminated by heating to about 70° C. and centrifuging the reaction mixture.

The glucuronides are isolated by HPLC under the following conditions: the sample is injected onto the 3.9 mm×30 cm μBondapak C18 column (Waters) and eluted for 10 min with 0.1% NH$_4$OAc (pH 7.5). After 10 min a linear gradient to 60% methanol is applied to the column over a 20 min period. The glucuronides are then collected free of contaminants. Tropic acid methyl ester glucuronide elutes at 28% methanol and p-hydroxyphenylacetic acid methyl ester glucuronide elutes at 20% methanol. Both glucuronides are identified by *E. coli* (Sigma, Type VII) β-glucuronidase hydrolysis. One ml of the glucuronide (OD=1) is added to 200 units *E. coli* β-glucuronidase in 50 mM phosphate buffer, pH 6.8, (10 μl) and incubated for 1 hr at 37° C. After hydrolysis, the compounds generated show retention times identical to tropic acid and p-hydroxyphenylacetic acid methyl esters, respectively, in the HPLC system described above.

EXAMPLE 3

Synthesis of Scopolamine p-Hydroxybenzoate

This example discloses the preparation of either scopolamine p-hydroxybenzoate or tropicamide p-hydroxybenzoate by use of either scopolamine hydrobromide or tropicamide as the respective starting material. The conditions of the process for making either p-hydroxybenzoate are otherwise the same.

Into a 250 ml erlenmeyer flask were charged 10 g (0.145 mol) p-hydroxybenzoic acid, 40 ml (23 g, 0.42 mol) acetic anhydride and 10 drops concentrated (36N) sulfuric acid. After heating for 0.5 hr at 55° C., the flask was removed from the bath and the contents allowed to cool to 35° C.; 200 ml distilled water was added and the slurry transferred to a beaker. An additional 200 ml of water were added, the mixture stirred for 5 min and then filtered. The filter cake was washed with water, and the solids were then dissolved in 200 ml warm absolute ethanol and 125 ml distilled water added. The slightly cloudy solution was heated until clear and the solution allowed to stand overnight. The solids which precipitated were filtered and vacuum oven dried. The O-acetyl p-hydroxybenzoate was recrystallized from ethyl ether (containing 2% ethanol)/petroleum ether yielding white platelets.

Into a predried 250 ml round bottom flask were charged 3.6 g (0.02 mol) O-acetyl-p-hydroxybenzoic acid, 6.14 g (0.016 mol) scopolamine hydrobromide, 0.3 g (0.002 mol) 4-pyrrolidinopyridine and 50 ml methylene chloride (dried over molecular sieves). To this stirred mixture was added 4.12 g (0.02 mol) N,N'-dicyclohexylcarbodiimide with the aid of 50 ml of methylene chloride. The flask was fitted with a condenser capped with a calcium sulfate drying tube and an oil bath maintained at 50°–55° C. used to heat the stirred mixture for 20 hr. The mixture was cooled, suction filtered through Celite and the solvent removed in vacuo. To the residue was added 150 ml water yielding a milky solution (pH ~4.75). This was extracted three times, 100 ml each, with ethyl ether. Sodium chloride was added to break the emulsion which formed. The pH of the aqueous layer was adjusted to 9.5 with 1.0N ammonium hydroxide and the oil which formed extracted into ethyl ether (3 times 100 ml). The combined ether layers were water-washed until the aqueous wash reached pH 8.0, the ether solution filtered, and the solvent removed in vacuo. The oily residue was taken up in 1:1 ethanol/water and the pH adjusted to 4.0–4.5 with 1.0 M hydrochloric acid. The solvents were removed in vacuo and residual water removed by repeatedly dissolving the product in absolute ethanol and removing the solvent in vacuo. The product was found to consist of an approximately 50/50 mixture of free and O-acetyl-blocked scopolamine p-hydroxybenzoate.

Into a predried 100 ml round bottom flask were charged 1.0 g (0.002 mol) of the mixture from above along with 40 ml dimethoxyethane (dried over molecular sieves). To the stirred, slightly cloudy solution was added 0.4 g (0.01 mol) sodium borohydride. The flask was capped with a condenser and drying tube and the stirred reaction mixture heated in an oil bath maintained at 25°–35° C. for 18 hr. The flask was then cooled in an ice-salt bath and 20 ml saturated aqueous ammonium chloride added in small increments. Ethyl ether (75 ml) was added and the resultant ether layer extracted with two 20 ml portions of saturated aqueous ammonium chloride and two 20 ml portions of saturated aqueous sodium chloride. The ether layer was dried over sodium sulfate and the solvent removed in vacuo. The resultant oil was converted to the hydrochloride salt as described above. NMR analysis confirmed the product to be scopolamine p-hydroxybenzoate. The crude product may be recrystallized from chloroform/ether.

Scopolamine p-hydroxybenzoate or tropicamide p-hydroxybenzoate is isolated by reverse phase chromatography in methanol/0.1% NH$_4$OAc, pH 7.5. The reaction mixture is evaporated to dryness in vacuo and resuspended in MeOH/0.1% NH$_4$OAc, pH 7.5 (1/1). The resulting colloidal suspension is loaded onto a 60 ml (15×250 mm) column packed with C-18 PrePAK (Waters) and equilibrated with 40% MeOH/60% 0.1% NH$_4$OAc. Scopolamine p-hydroxybenzoate or tropicamide p-hydroxybenzoate is isolated by step elution with 2 column volumes of 40% MeOH, 50% MeOH, 60% MeOH, and 70% MeOH. The fraction containing scopolamine p-hydroxybenzoate or tropicamide p-hydroxybenzoate is dryed in vacuo.

EXAMPLE 4

Synthesis of Tropicamide p-Hydroxybenzoyl-O-β-D-Glucuronic Acid (See Chart 2)

The glucuronide of tropicamide p-hydroxybenzoate is synthesized with uridine 5'-diphosphoglucuronic acid transferase as described in Example 2. Due to the low solubility of this compound, excess solid material is added to the reaction mixture so that a saturated solution of aglycon is maintained throughout the reaction. The glucuronide is isolated by HPLC with the reversed phase system described in Example 2. It is characterized by hydrolysis with excess *E. coli* β-glucuronidase (1000 U/ml, pH 6.8) (Sigma, Type VIII) for 1 hr at 37° C. which quantitatively releases the aglycon as assayed by HPLC.

EXAMPLE 5

Synthesis of Scopolamine
p-Hydroxybenzoy-O-β-D-Glucuronic Acid (See Chart 2)

The glucuronide of scopolamine p-hydroxybenzoate is synthesized with uridine 5'-diphosphoglucuronic acid transferase by first removing all or substantially all of the esterase activity from liver microsomes. These esterases are removed since they will hydrolyze the aglycon. This operation can be done by washing the liver microsomes in a suitable buffer, as described herein, or by other equivalent washing means known to persons in this art. Advantageously, an esterase inhibitor can be used to supplement the washing of the microsomes. For example, a competitive inhibitor of the esterases such as lysine ethyl ester, and the like, or a suicide substrate such as phenylmethylsulfonyl fluoride, and the like, can be used. Due to the low solubility of scopolamine p-hydroxybenzoate, excess solid material is added to the reaction mixture so that a saturated solution of aglycon is maintained throughout the reaction. The aglycon is first dissolved at a concentration of ~0.5 mg/ml in 75 mM Tris.HCl pH=7.0 containing 10 mM $MgCl_2$. Resuspended enzyme is added to a final concentration of 0.08 U/ml and UDPGA is added to a concentration of 4 mg/ml. The reaction is carried out at 37° C. for 1 hr after which the microsomes are removed by centrifugation. The glucuronide is isolated by HPLC with the reversed phase system described in Example 2 with the exception that the 0.1% $NH_4OAc$ solution is pH 4.0. The glucuronide is characterized by hydrolysis with excess *E. coli* β-glucuronidase (100 U/ml, pH 6.8) (Sigma, Type VII) for 1 hr at 37° C. which quantitatively releases the aglycon as assayed by HPLC.

EXAMPLE 6

Preparation of Hyoscyamine
p-Hydroxybenzoyl-O-β-D-Glucuronic Acid

The reaction conditions are identical to those utilized for scopolamine in Examples 3 and 5 except for the substitution of hyoscyamine for scopolamine.

EXAMPLE 7

Preparation of Atropine
p-Hydroxybenzoyl-O-β-D-Glucuronic Acid

The reaction conditions are identical to those utilized for scopolamine in Examples 3 and 5 except for the substitution of atropine for scopolamine.

EXAMPLE 8

Preparation of Scopolamine N-Oxide
p-Hydroxybenzoyl-O-β-D-Glucuronic Acid

The reaction conditions are identical to those utilized for scopolamine in Examples 3 and 5 except for the substitution of scopolamine N-oxide for scopolamine.

EXAMPLE 9

Preparation of Eucatropine
p-Hydroxybenzoyl-O-β-D-Glucuronic Acid

The reaction conditions are identical to those utilized for scopolamine in Examples 3 and 5 except for the substitution of eucatropine for scopolamine.

EXAMPLE 10

Preparation of Homatropine
p-Hydroxybenzoyl-O-β-D-Glucuronic Acid

The reaction conditions are identical to those utilized for scopolamine in Examples 3 and 5 except for the substitution of homatropine for scopolamine.

EXAMPLE 11

Preparation of Procyclidine
p-Hydroxybenzoyl-O-β-D-Glucuronic Acid

The reaction conditions are identical to those utilized for scopolamine in Examples 3 and 5 except for the substitution of procyclidine for scopolamine.

EXAMPLE 12

Glucuronides of other phenolic anticholinergics, or phenolic derivatives of other anticholinergics, within the scope of this invention, can be prepared by following the procedures of Example 5 with the appropriate substitution of other anticholinergic compounds for scopolamine p-hydroxybenzoate.

EXAMPLE 13

Salts with both inorganic and organic bases can be formed with the free acid of the compounds of the subject invention. For example, in addition to the ammonium salt, there also can be formed the sodium, potassium, calcium, and the like salts, by neutralizing an aqueous solution of the free acid with the corresponding base. The ammonium and other base salts of the compounds of the subject invention are useful in the same manner as the free acid form.

Formulations for antiperspirant use

The concentration of anticholinergic glucuronide or base addition salt employed in topical compositions for application to the human body should be consistent with the requirements of efficacy, safety and economy. These requirements can often be met with extremely small amounts of active ingredient, e.g., a small but perceptible amount of as little as about 0.01% by weight. We prefer to employ from about 0.01 to about 2% by weight. As indicated heretofore, the present compositions can include the aforementioned principal active ingredients either alone or in combination with other active materials. Accordingly, other antiperspirants such as the aluminum salts, zinc salts and zirconium salts (e.g., the chlorides, chlorhydroxides and sulfates) in concentrations of from about 5 to about 25 percent can be employed as supplementary active ingredients. Additionally, combinations of the said principal active ingredients with antibacterial agents suitable for topical deodorant use without inactivating glucuronidase offer a balanced approach to the problem. Such combinations include substances capable of minimizing bacterial action on available organic secretions in the affected areas, thereby supplementing the primary activity. The known antibacterials with demonstrated effectiveness in this function are appropriate for use in the present compositions.

Dermatologically acceptable carriers into which the active ingredients can be incorporated to produce satisfactory antiperspirant compositions, as indicated heretofore, are those commonly employed for topical application of cosmetics or pharmaceuticals. Such carriers or vehicles include lotions, ointments aerosols, water solutions, creams (preferably of the oil-in-water type), pulverulent mixtures, gelled sticks and the like. Depending on the physical nature of the vehicle or carrier employed, the method of this invention can be practiced by applying such compositions topically from a roll-on applicator, by a brush or pad, by sprinkling on the skin, from a squeeze bottle, by spraying under propellant pressure, and in other manners according to the particular type of carrier employed.

In preparing the desired product form of the present compositions, various additives, diluents and adjuvants can be utilized. These illustratively include perfumes, essential oils, surfactants (e.g. polysorbate 80, polyoxyethylene sorbitan trioleate, sodium lauryl sulfate, sodium cetyl sulfate), emulsifiers, (e.g., glyceryl monostearate-diethylaminoethyl alkyl amide phosphate, isopropyl myristate, cetyl alcohol, glyceryl and glycol esters of stearic acid), alcohols (e.g., ethanol and isopropanol), glycols (e.g., propylene glycol, glycerol, sorbitol), ointment-type bases (e.g., spermaceti, carbowaxes, beeswax), higher fatty acids (e.g., stearic acid, palmitic acid), propellants (e.g., halogenated hydrocarbons, carbon dioxide, nitrogen), silicone-type fluids (e.g., polysiloxane fluid), and solid diluents (e.g. calcium carbonate, starch, bentonite, talc).

The following Composition examples disclose formulations with the compounds of this invention denoted as "active antiperspirant compound."

EXAMPLE 14

Cream Antiperspirant Composition

A cream antiperspirant composition is prepared by mixing together the ingredients of the following recipe in which the parts are by weight.

| Ingredient | Parts |
| --- | --- |
| Condensate of ethylene oxide with a hydrophobic base formed by condensing propylene oxide with propylene glycol (Pluronic F-68) | 5.0 |
| Active antiperspirant compound | 1.0 |
| Cetyl trimethyl ammonium bromide | 0.5 |
| Cetyl alcohol | 1.0 |
| Glyceryl monostearate | 13.0 |
| Spermaceti wax | 4.0 |
| Glycerine | 3.0 |
| Polyoxyalkylene propylene glycol monostearate | 0.5 |
| Polyoxyalkylene stearate | 0.5 |
| Ethanol | 10.0 |
| Perfume | 0.1 |
| Water, q.s. | 100 gm |

The foregoing composition when used daily is effective in reducing axially perspiration. Repeated applications have less tendency to cause irritation to the skin than do similar compositions containing conventional astringent antiperspirants, similarly causing less irritation when applied to freshly shaved areas of the skin.

EXAMPLE 15

Lotion Antiperspirant Composition

The following lotion composition is prepared in which the parts are by weight:

| Ingredient | Parts |
| --- | --- |
| Condensate of ethylene oxide with a hydrophobic base formed by condensing propylene oxide with propylene glycol (Pluronic F-68) | 10.0 |
| Active antiperspirant compound | 2.0 |
| 8-Hydroxyquinoline sulfate | 0.8 |
| Ethanol | 5.0 |
| Veegum | 3.5 |
| Mineral oil | 6.0 |
| Stearyl alcohol | 1.5 |
| Polyoxyalkylene propylene glycol monostearate | 0.8 |
| Polyoxyalkylene stearate | 0.8 |
| Perfume | 0.1 |
| Water, q.s. | 100 gm |

The composition when applied to the skin produces results similar to those obtained with the composition of Example 14.

EXAMPLE 16

Liquid Antiperspirant Composition

The following liquid antiperspirant composition is prepared in which the parts are by weight.

| Ingredient | Parts |
| --- | --- |
| Condensate of ethylene oxide with a hydrophobic base formed by condensing propylene oxide with propylene glycol (Pluronic F-68) | 10.0 |
| Active antiperspirant compound | 0.05 |
| Aluminum chlorhydrol | 10.00 |
| Glycerine | 5.0 |
| Ethanol | 32.0 |
| Benzyl-dimethyl-alkyl ammonium chloride containing 8 to 18 carbon atoms in the alkyl group | 0.1 |
| Perfume | 0.1 |
| Water, q.s. | 100 gm |

When the composition is applied to the skin, the results obtained are similar to those obtained with the composition of Example 14.

EXAMPLE 17

Antiperspirant Stick Deodorant

An antiperspirant (and deodorant) in stick form is prepared by mixing together the following ingredients at elevated temperature, then pouring the composition into a mold and allowing it to solidify. The quantity of each ingredient in parts by weight is given below:

| Ingredient | Parts |
| --- | --- |
| Condensate of ethylene oxide with a hydrophobic base formed by condensing propylene oxide with propylene glycol (Pluronic F-68) | 2.0 |
| Active antiperspirant compound | 2.0 |
| Sodium stearate | 0.5 |
| Propylene glycol | 8.5 |
| Cetyl trimethyl ammonium bromide | 5.0 |
| Perfume | 0.5 |
| Ethyl alcohol, q.s. | 0.1 |
| | 100 gm |

When rubbed on the skin, the stick provides similar results as were obtained with the composition of Example 14.

EXAMPLE 18

Aerosol Antiperspirant

| Ingredient | Parts |
|---|---|
| Aluminum chlorhydrol | 11.9 |
| Active antiperspirant compound | 2.0 |
| Isopropyl myristate | 2.0 |
| Volatile silicone | 11.0 |
| Bentone | 1.0 |
| Ethyl alcohol | 2.0 |
| Perfume | 0.1 |

The above composition is packaged in a pressure container in the conventional manner along with 78 parts of a conventional liquified gaseous propellant.

When the liquid is sprayed upon the skin in the usual manner upon release from the pressurized package, it is found to be effective as an antiperspirant in the same manner as the composition of the preceding examples.

While particular embodiments of the invention have been described, it will be apparent to those skilled in the art that variations may be made thereto without departing from the spirit of the invention and the scope of the appended claims.

TABLE 1

| | Hydrolysis of Glucuronides (nmoles/hour/100 units) | | |
|---|---|---|---|
| Enzyme Source: (pH) | E. coli 6.8 | Bovine liver (5.0) | Dialyzed Human Sweat (5.0) |
| Aglycon: | | | |
| Phenolphthalein | 200 | 200 | 200 |
| Tropicamide | >150 | 24 | 1.6 |
| Scopolamine | 60 | 25 | <0.5 |
| Tropic acid methyl ester | — | — | 2.6 |
| p-Hydroxyphenylacetic acid methyl ester | — | — | 37 |
| Tropicamide p-hydroxybenzoate | — | — | 36 |
| Scopolamine p-hydroxybenzoate | — | — | 40 |

TABLE 2

| Comparison of Mydriatic Potential of Anticholinergics and Anticholinergic Glucuronides | | |
|---|---|---|
| | Amt. of drug applied | Change in Pupil Diameter* as a function of time |
| Tropicamide | 20 ug | 1 mm in 35 min |
| | 600 ug | 7 mm in 20 min |
| Scopolamine | 0.6 ug | 0 mm in 15 min |
| | 6 ug | 6 mm in 15 min |
| | 60 ug | 6 mm in 10 min |
| Tropicamide glucuronic acid | 600 ug | 0 mm in 30 min |
| Tropicamide p-hydroxybenzoate | 5.5 ug | 4 mm in 35 min |
| Tropicamide p-hydroxybenzoate glucuronic acid | 600 ug | 0 mm in 25 min |
| Scopolamine p-hydroxybenzoate | 0.1 ug | 7 mm in 15 min |
| Scopolamine p-hydroxybenzoate glucuronic acid | 11.4 ug | 0 mm in 45 min |

*Error ± 0.5 mm

CHART 1

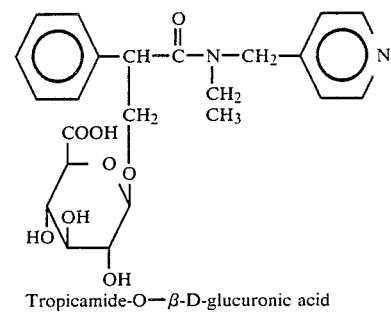

Tropicamide-O—β-D-glucuronic acid

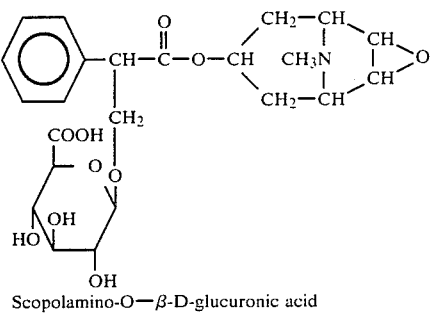

Scopolamino-O—β-D-glucuronic acid

CHART 2

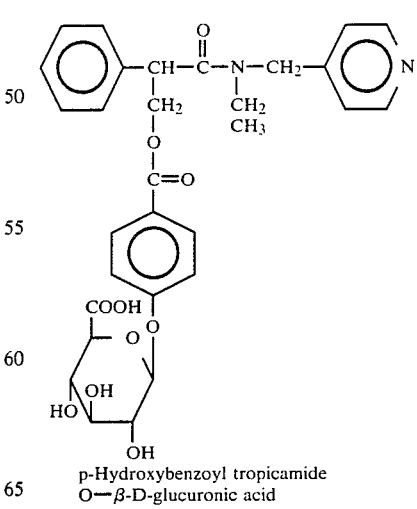

p-Hydroxybenzoyl tropicamide O—β-D-glucuronic acid

-continued
CHART 2

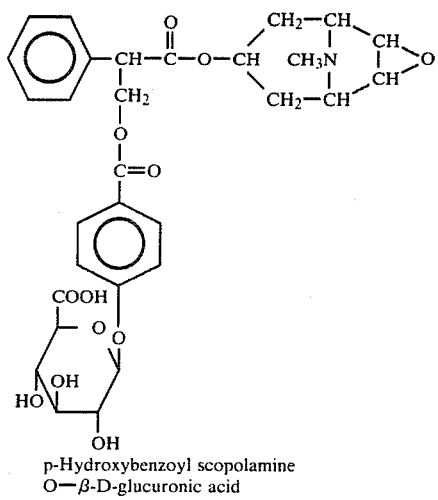

p-Hydroxybenzoyl scopolamine
O—β-D-glucuronic acid

CHART 3

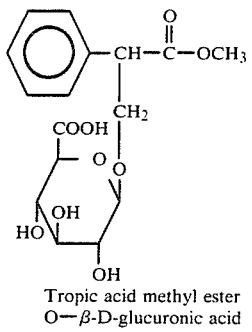

Tropic acid methyl ester
O—β-D-glucuronic acid

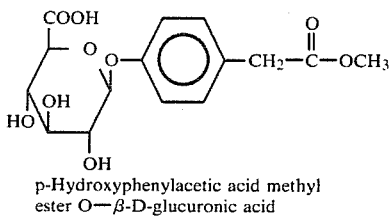

p-Hydroxyphenylacetic acid methyl
ester O—β-D-glucuronic acid

We claim:

1. The 1-O-β-D-glucuronic acid of an anticholinergic compound that possesses a single phenolic moiety; and base addition salts thereof.

2. The 1-O-β-D-glucuronic acid of an anticholinergic compound that possesses a single phenolic moiety, according to claim 1, wherein said compound is selected from the group consisting of p-hydroxybenzoyl scopolamine; p-hydroxybenzoyl tropicamide; para, meta, or ortho hydroxylated scopolamine, atropine, scopolamine N-oxide, eucatropine, homatropine, and procyclidine; and para, meta, or ortho hydroxylated derivatives of aliphatic and aromatic fatty acid esters of scopolamine; and base addition salts thereof.

3. Tropicamide p-hydroxybenzoyl-O-β-D-glucuronic acid, a compound according to claim 1.

4. Scopolamine p-hydroxybenzoyl-O-β-D-glucuronic acid, a compound according to claim 1.

5. Atropine p-hydroxybenzoyl-O-β-D-glucuronic acid, a compound according to claim 1.

6. Scopolamine N-oxide p-hydroxybenzoyl-O-βD-glucuronic acid, a compound according to claim 1.

7. Eucatropine p-hydroxybenzoyl-O-β-D-glucuronic acid, a compound according to claim 1.

8. Procyclidine p-hydroxybenzoyl-O-β-D-glucuronic acid, a compound according to claim 1.

9. p-Hydroxyscopolamine-O-β-D-glucuronic acid, a compound according to claim 1.

10. n-Hexanoyl p-hydroxyscopolamine-O-β-D-glucuronic acid, a compound according to claim 1.

11. 2-Ethylbutyrl p-hydroxyscopolamine N-oxide-O-β-D-glucuronic acid, a compound according to claim 1.

12. An antiperspirant composition comprising from about 0.01% to about 2% by weight of an antiperspirant compound consisting of the 1-O-β-D-glucuronic acid of an anticholinergic compound that possesses a single phenolic moiety; and base addition salts thereof, incorporated into a dermatologically acceptable carrier.

13. An antiperspirant composition, according to claim 12, wherein the active antiperspirant compound is the 1-O-β-D-glucuronic acid of an anticholinergic compound that possesses a single phenolic moiety, wherein said active antiperspirant compound is selected from the group consisting of p-hydroxybenzoyl scopolamine; p-hydroxybenzoyl tropicamide; para, meta, or ortho hydroxylated scopolamine, atropine, scopolamine N-oxide, eucatropine, homatropine, and procyclidine; and para, meta, or ortho hydroxylated derivatives of aliphatic and aromatic fatty acid esters of scopolamine; and base addition salts thereof, incorporated into a dermatologically acceptable carrier.

14. An antiperspirant composition as described in claim 12, in which the carrier is selected from the group comprising lotions, ointments, aerosols, water solutions, creams, pulverulent mixtures, and gelled sticks.

15. The process of inhibiting perspiration which comprises the step of applying to the human body a composition comprising from about 0.01% to about 2% by weight of an antiperspirant compound selected from the group consisting of the 1-O-β-D-glucuronic acid of an anticholinergic compound that possesses a single phenolic moiety; and base addition salts thereof, incorporated into a dermatologically acceptable carrier.

16. The process of inhibiting perspiration as described in claim 15, in which the antiperspirant compound is the 1-O-β-D-glucuronic acid of an anticholinergic compound that possesses a single phenolic moiety, wherein said compound is selected from the group consisting of p-hydroxybenzoyl scopolamine; p-hydroxybenzoyl tropicamide; para, meta, or ortho hydroxylated scopolamine, atropine, scopolamine N-oxide, eucatropine, homatropine, and procyclidine; and para, meta, or ortho hydroxylated derivatives of aliphatic and aromatic fatty acid esters of scopolamine; and base addition salts thereof, incorporated into a dermatologically acceptable carrier.

17. The process of inhibiting perspiration as described in claim 15 in which the carrier is selected from the group comprising lotions, ointments, aerosols, water solutions, creams, pulverulent mixtures, and gelled sticks.

* * * * *

UNITED STATES PATENT AND TRADEMARK OFFICE
CERTIFICATE OF CORRECTION

PATENT NO. : 4,546,096

DATED : October 8, 1985

INVENTOR(S) : Walter C. Herlihy, David M. Epstein, Carl B. Felger

It is certified that error appears in the above-identified patent and that said Letters Patent are hereby corrected as shown below:

Col. 1, line 62: "scopolamine p-hydroxybenzoyl" should read --scopolamine; p-hydroxybenzoyl--.
Col. 1, line 63: "tropicamide:" should read --tropicamide;--.
Col. 1, line 65: "like:" should read --like;--.
Col. 2, line 67: "wa" should read --was--.
Col. 3, line 64: "detectable therefore" should read --detectable; therefore--.
Col. 7, line 4: "p-Hydroxybenzoy-" should read --p-Hydroxybenzoyl- --.
Col. 7, line 25: "Tris.HCL" should read --Tris·HCl--.
Col. 8, line 67: "ointments aerosols" should read --ointments, aerosols--.
Col. 9, line 53: "axially" should read --axillary--.
Col. 11, line 22: "composition" should read --compositions--.
Col. 12, lines 20 and 37: "O--β-D-" should read -- O-β-D- --.
Col. 12, line 37: "Scopolamino-" should read --Scopolamine--.
Col. 12, line 65: "O--β-D-" should read --O-β-D- --.
Col. 13, line 22: "O--β-D-" should read --O-β-D- --.
Col. 13, line 38: "O--β-D-" should read --O-β-D- --.
Col. 13, line 47: "O--β-D-" should read --O-β-D- --.
Col. 14, Claim 6, line 5: "-O-βD-" should read --O-β-D- --.

Signed and Sealed this

Eighteenth Day of February 1986

[SEAL]

Attest:

DONALD J. QUIGG

Attesting Officer   Commissioner of Patents and Trademarks